US011435313B2

(12) United States Patent
Atkins et al.

(10) Patent No.: US 11,435,313 B2
(45) Date of Patent: Sep. 6, 2022

(54) COAL-BASED GRAPHENE BIOSENSORS

(71) Applicant: CARBON HOLDINGS INTELLECTUAL PROPERTIES, LLC, Sheridan, WY (US)

(72) Inventors: Charles Agee Atkins, Sheridan, WY (US); Garrett W. Lindemann, Buffalo, WY (US)

(73) Assignee: CARBON HOLDINGS INTELLECTUAL PROPERTIES, LLC, Ranchester, WY (US)

(*) Notice: Subject to any disclaimer, the term of this patent is extended or adjusted under 35 U.S.C. 154(b) by 0 days.

(21) Appl. No.: 16/827,615

(22) Filed: Mar. 23, 2020

(65) Prior Publication Data
US 2020/0240949 A1 Jul. 30, 2020

Related U.S. Application Data

(63) Continuation-in-part of application No. 16/230,318, filed on Dec. 21, 2018, now Pat. No. 10,889,500.
(Continued)

(51) Int. Cl.
*G01N 27/414* (2006.01)
*C01B 32/184* (2017.01)
(Continued)

(52) U.S. Cl.
CPC ....... *G01N 27/4145* (2013.01); *C01B 32/184* (2017.08); *G01N 27/4146* (2013.01); *G01N 33/5302* (2013.01); *G01N 33/574* (2013.01)

(58) Field of Classification Search
CPC ........... G01N 27/4145; G01N 33/5302; G01N 33/574; G01N 27/4146; C01B 32/184;
(Continued)

(56) References Cited

U.S. PATENT DOCUMENTS 3,639,953 A 2/1972 Kimura et al.
4,439,304 A 3/1984 Sudbury et al.
(Continued)

FOREIGN PATENT DOCUMENTS

CN 105836739 A 8/2016
WO 2011004136 A1 1/2011

OTHER PUBLICATIONS

Lin, Hongjun, et al. "Modified enzyme-linked immunosorbent assay strategy using graphene oxide sheets and gold nanoparticles functionalized with different antibody types." Analytical chemistry 85.13 (2013): 6228-6232.*
(Continued)

*Primary Examiner* — Richard M Rump
(74) *Attorney, Agent, or Firm* — Dorsey & Whitney LLP

(57) ABSTRACT

An example method includes providing coal and extracting the graphene from the coal. The graphene may be extracted using any suitable technique, such as the Hummers method, a modified Hummers method, or exfoliation of graphite. The graphene may include impurities or other electrical properties that depend at least partially on the composition of the coal. The method may further include forming a life science device from the graphene. The life science device may include, for example, a biosensor or a drug delivery system.

20 Claims, 5 Drawing Sheets

Related U.S. Application Data

(60) Provisional application No. 62/822,206, filed on Mar. 22, 2019.

(51) Int. Cl.
   *G01N 33/53* (2006.01)
   *G01N 33/574* (2006.01)

(58) Field of Classification Search
   CPC ............ C01B 2204/04; C01B 2204/30; C01B 2204/32; C01B 2204/22; C01B 2204/24; C01B 32/194; C01B 32/192
   See application file for complete search history.

(56) References Cited

U.S. PATENT DOCUMENTS

| | | | |
|---|---|---|---|
| 4,804,390 | A | 2/1989 | Lloyd et al. |
| 5,692,807 | A | 12/1997 | Zimmerman |
| 8,148,435 | B2 | 4/2012 | Fiato |
| 9,074,138 | B2 | 7/2015 | Rinker |
| 9,676,621 | B2 * | 6/2017 | Chen ................. G01N 27/4145 |
| 2007/0196239 | A1 * | 8/2007 | Vink .................. G01N 21/6428 422/82.05 |
| 2009/0061193 | A1 | 3/2009 | Hara et al. |
| 2011/0011719 | A1 | 1/2011 | Rinker |
| 2012/0076703 | A1 | 3/2012 | Stiller et al. |
| 2014/0120030 | A1 | 5/2014 | Kim et al. |
| 2014/0223882 | A1 | 8/2014 | Shah et al. |
| 2014/0242262 | A1 | 8/2014 | Briman et al. |
| 2015/0329363 | A1 | 11/2015 | Sullivan |
| 2016/0060122 | A1 | 3/2016 | Tour et al. |
| 2017/0198221 | A1 | 7/2017 | Targett et al. |
| 2018/0155201 | A1 | 6/2018 | Zhang |

OTHER PUBLICATIONS

Zhou, Quan, et al. "Graphene sheets from graphitized anthracite coal: preparation, decoration, and application." Energy & fuels 26.8 (2012): 5186-5192.*

Singh, B. G. P., et al. "Carbon nanotubes. A novel drug delivery system." International Journal of Research in Pharmacy and Chemistry 2.2 (2012): 523-532.*

Hossain, Md Faruk, and Jae Y. Park. "Fabrication of sensitive enzymatic biosensor based on multi-layered reduced graphene oxide added PtAu nanoparticles-modified hybrid electrode." PLoS One 12.3 (2017): e0173553.*

Deng, Shikai, et al. "Graphene wrinkles enable spatially defined chemistry." Nano letters 19.8 (2019): 5640-5646.*

Andresen, John M., et al. "Synthesis of pitch materials from hydrogenation of anthracite." Fuel processing technology 85.12 (2004): 1361-1372.

International Search Report and Written Opinion for PCT Application No. PCT/US2018/067341, dated May 23, 2019.

International Search Report and Written Opinion for PCT Application No. PCT/US2018/067351, dated May 2, 2019.

Li, Gang, et al. "One-step green synthesis of nitrogen and phosphorus co-doped pitch-based porous graphene-like carbon for supercapacitors." Journal of Porous Materials 24.6 (2017): 1689-1696.

IUPAC. Compendium of Chemical Terminology, 2nd ed. (the "Gold Book"). Compiled by A. D. McNaught and A. Wilkinson. Blackwell Scientific Publications, Oxford (1997)., Online version (2019-) created by S. J. Chalk. ISBN 0-9678550-9-8. https://doi.org/10.1351/goldbook.

Kim, et al., "Pitch-Based Carbon Fibers From Coal Tar or Petroleum Residue Under the Same Processing Condition", Carbon Letters vol. 19, Jun. 14, 2016, 72-78.

Ye, Ruquan et al., "Bandgap engineering of coal-derived graphene quantum dots. (Supporting Information)" ASC applied materials & interfaces 7.12 (2015): S1-S5.

International Search Report and Written Opinion received for International Application No. PCT/US2020/024334, dated Jun. 16, 2020, 8 pages.

Kumar, et al., "Facile Synthesis of Few Layer Graphene From Bituminous Coal and its Application Towards Electrochemical Sensing of Caffeine", Advanced Materials Letters, vol. 8, No. 3, pp. 239-245, Feb. 2017, VBRI Press.

* cited by examiner

COAL-BASED GRAPHENE BIOSENSORS

CROSS-REFERENCE TO RELATED APPLICATION

This application claims priority to U.S. Provisional Application No. 62/822,206 filed on Mar. 22, 2019, and is a continuation-in-part of U.S. patent application Ser. No. 16/230,318, filed Dec. 21, 2018, the disclosures of which are incorporated herein, in their entireties, by this reference.

FIELD

The described embodiments relate generally to sensors, and more particularly to coal-based graphene biosensors.

BACKGROUND

Biosensors may be used in life sciences, clinical diagnostics, environmental monitoring, and medical research for affinity-based sensing, such as hybridization between complementary single strand DNA in a microarray or affinity binding of a matched sensitive biological element-antigen pair. Biosensors may include a biological recognition element and a transducer that converts a recognition event into a measurable electronic signal. While graphene has desirable electrical properties that can allow for its use in converting a biological recognition event into a measurable electronic signal, it can be expensive to produce and difficult to effectively functionalize or incorporate into usable technologies.

Accordingly, it may be desirable to provide a more economical method for producing graphene to allow for the production of less expensive sensors at a large scale. Further, unique properties of coal-based graphene as compared to other forms of graphene can enhance the functionality of biosensors and biosensor arrays.

SUMMARY

Embodiments disclosed herein relate to methods of forming graphene from coal for one or more life science devices, methods of forming the one or more life science devices that include graphene formed from coal, and the related life science devices. An example method includes providing coal and extracting the graphene from the coal. The graphene may be extracted using any suitable technique, such as the Hummers method, a modified Hummers method, or exfoliation of graphite. The method may further include forming a life science device from the graphene. The life science device may include, for example, a biosensor or a drug delivery system.

In an embodiment, a method to form a life science device is disclosed. The method includes providing graphene formed from coal and forming a life science device from the graphene.

In some embodiments, forming the life science device from the graphene includes disposing at least one graphene layer that includes the graphene on a substrate to form a biosensor. The at least one graphene layer includes one or more binding sites configured to bind or otherwise react with one or more targets.

In some embodiments, disposing the at least one graphene layer on the substrate includes disposing at least one first graphene layer on the substrate to form at least one first subsensor and at least one second graphene layer on the substrate to form at least one second subsensor that is spaced from the at least one first subsensor. The at least one first graphene layer includes one or more first binding sites and the at least one second graphene layer includes one or more second binding sites that are different than the one or more first binding sites.

In some embodiments, the method includes forming one or more electrical contacts on at least one of the at least one graphene layer or the substrate.

In some embodiments, the method includes functionalizing the graphene to form the one or more binding sites.

In some embodiments, the method includes attaching, either directly or indirectly, one or more sensitive biological elements to the at least one graphene layer.

In some embodiments, forming the life science device from the graphene includes rolling the graphene into a carbon nanotube to form a drug delivery system.

In some embodiments, providing the graphene formed from coal includes providing the coal and extracting the graphene from the coal.

In an embodiment, a method of forming graphene from coal that is suitable for use in one or more life science devices is disclosed. The method includes providing the coal and extracting the graphene from the coal.

In some embodiments, extracting the graphene from the coal includes extracting the graphene from the coal using the Hummers method or a modified Hummers method.

In some embodiments, extracting the graphene from the coal includes exfoliating graphite that is present in the coal.

In some embodiments, the method includes evaluating the coal to determine one or more characteristics of the coal.

In some embodiments, the one or more characteristics include at least one of a carbon, aromaticity, heavy metal, or ash content of the coal.

In some embodiments, one or more parameters of an extraction technique that is used to extract the graphene from the coal is selected at least in part in response to analyzing the coal.

In some embodiments, the method includes, after extracting the graphene from the coal, evaluating the graphene to determine one or more characteristics of the graphene.

In some embodiments, the one or more characteristics includes at least one of average flake size, graphene purity, average number of carbon layers, presence of impurities, composition of the impurities, electrical properties, or thermal properties.

In some embodiments, the method includes selecting graphene exhibiting one or more selected characteristics for use in the one or more life science devices.

In some embodiments, the method further includes functionalizing the graphene.

In some embodiments, the method includes forming the graphene into one or more life science devices.

In an embodiment, a biosensor is disclosed. The biosensor includes a substrate, at least one graphene layer disposed on the substrate, and one or more binding sites on the graphene that is configured to bind or otherwise react with one or more targets. The at least one graphene layer includes graphene formed from coal.

In some embodiments, the biosensor includes at least one first subsensor and at least one second subsensor spaced from the at least one first subsensor. The at least one first subsensor including one or more first binding sites and the at least one second subsensor includes one or more second binding sites that are different than the one or more first binding sites.

In some embodiments, the biosensor is at least one of an amperometric biosensor, a conductometric biosensor, a potentiometric biosensor, impedimetric biosensor or a field-effect transistor biosensor.

In some embodiments, wherein the biosensor is at least one of a rapid diagnostic biosensor, a sequencing biosensor, a cancer detection biosensor, or a biosensor for personalized medicine.

In some embodiments, the biosensor is an enzyme-linked immunosorbent assay.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1:
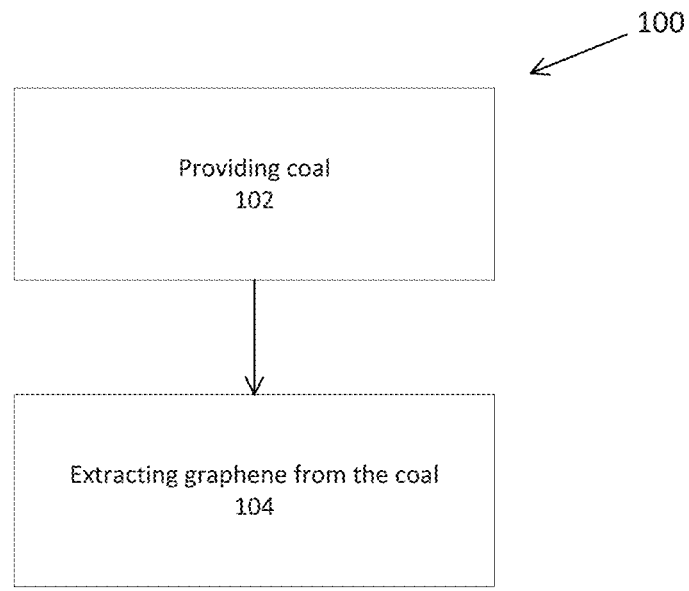
FIG. 1 is a flow chart of a method of forming graphene for one or more life science devices.

The present disclosure relates to methods of forming graphene from coal, for example for use in one or more life science devices, methods of forming one or more life science devices that include graphene formed from coal, graphene formed from coal and comprising one or more elements or contaminants present in the source coal, and related life science devices. An example method includes providing coal and forming graphene from at least some of the coal. The graphene may be extracted or formed using any suitable technique, such as the Hummers method, a modified Hummers method, or exfoliation of graphite formed from the coal. The method may further include forming a life science device from or including the graphene. The life science device may include, for example, a biosensor or a drug delivery system.

Conventionally, graphene formed using chemical vapor deposition ("CVD") can be used in life science devices, for example as a substrate for a biosensor. Many studies have demonstrated that graphene produced by CVD, especially chemically modified graphene ("CMG"), can interface with individual whole cells, groups of cells, and biological components of cells. Graphene produced by CVD may be used as a biosensor detection device and/or a drug delivery system thereby allowing for life science research, biomedicine, and personalized medicine to be carried out using relatively small-scale devices that can be highly affordable and transportable. However, graphene produced using CVD can be extremely expensive and can be too expensive to use for most applications, including use in life science devices. Further, chemically modifying the graphene formed using CVD may negatively affect the electrical properties of the graphene, inhibiting the performance of a biosensor including the graphene.

Graphene derived from coal can be significantly cheaper than graphene formed using CVD and a conventional carbon source. Further, graphene derived from coal can exhibit several unique properties relative to graphene formed using other carbon sources. For example, graphene derived from coal may exhibit electrical, thermal, strength, and nano-scale properties that differ from graphene formed using other sources. The different properties of the graphene derived from coal can be due the large aromatic carbon molecules (including graphene) that naturally exist in coal and the incorporation of some hexavalent metals present in the coal into the structure of the graphene. For instance, the hexavalent metals may allow for at least one of quicker, easier, or more efficient functionalization of the graphene derived from coal without negatively affecting the electronic characteristics of the graphene as compared to conventionally formed graphene. Some sources of coal that include hexavalent metals (e.g., subbituminous coal, such as subbituminous coal from the Powder River Basin), compared to conventionally produced graphene, can produce a graphene that can be superior in electrical properties when functionalized by having less background noise, and that can also be easier, simpler, or quicker to functionalize. Coal, including low quality coal, may produce graphene exhibiting high quality, but low cost, and unique properties.

The advantages of using coal as a feedstock for life science devices are that it is in great abundance, graphene is naturally occurring as part of the composition, and the source is inexpensive. Since, graphene sensors can comprise a single layer of graphene on a metal substrate, extracting tens to a few hundred pounds of graphene per ton of coal (e.g., the graphene may not necessarily be efficiently extracted from the coal) can be enough to manufacture mass quantities graphene biosensors and/or manufacture a sufficient quantity of dosages of a carbon nanotube drug delivery system.

FIG. 1 is a flow chart of a method 100 of forming graphene from coal, for example for use in one or more life science devices (e.g., one or more biosensors or one or more graphene-based drug delivery systems), according to some embodiments. As shown in FIG. 1, the method 100 includes providing coal at block 102. The method 100 also includes extracting graphene from the coal at block 104. In some examples, one or more of the blocks 102 and/or 104 may be performed in a different order, eliminated, divided into additional acts, modified, supplemented with other acts, or combined into fewer acts.

Block 102 includes providing coal. Block 102 may include providing any suitable coal. For example, block 102 includes providing at least one of lignite, sub-bituminous coal, bituminous coal, or anthracite. In an embodiment, block 102 includes providing subbituminous coal from the Powder River Basin since such subbituminous coal may include desirable impurities, such as hexavalent metals, which may make functionalizing the graphene formed from such coal easier and/or cause the graphene to exhibit improve properties (e.g., electrical properties) compared to graphene formed from conventional carbon sources. As used herein with respect to coal and/or graphene, the term impurities can refer to any non-carbon element present in the coal and/or graphene and should not be interpreted as indicating that the presence of such an element is undesirable.

In an embodiment, the method 100 may include preparing the coal. In some examples, preparing the coal may include reducing the particle size of the coal to form a coal powder. For example, preparing the coal may include reducing the particle size of the coal so the coal exhibits an average particles size about 1 cm or less, about 7.5 mm or less, about 5 mm or less, about 2.5 mm or less, about 1 mm or less, about 750 μm or less, about 500 μm or less, about 250 μm or less, about 100 μm or less, about 75 μm or less, about 50 μm or less, about 25 μm or less, about 10 μm or less, about 5 μm or less, or about 1 μm or even less. Reducing the particle size of the coal may decrease the time and/or energy required to extract the graphene from the coal by reducing the volume of each coal particle and increasing the total surface area of the coal. In an example, preparing the coal may include sieving the coal so the coal exhibits a selected particle size or less. Similar to reducing the particle size of the coal, sieving the coal may ensure that the coal is free of large particles which may make extracting the graphene more difficult. In some examples, preparing the coal may include drying the coal to remove moisture therefrom since the moisture may decrease the controllability of block 104 by diluting any acid or chemical used. In some examples, preparing the coal includes a combination of the above examples. In some examples, preparing the coal can include heating the coal at one or more desired temperatures for one or more desired durations. In some examples, preparing the coal can include exerting a pressure on, or compressing the coal in one or more desired directions which can increase the graphene percentage.

In some examples, the method 100 may include evaluating the coal provided in block 102 to detect one or more characteristics of the coal. The characteristics of the coal that may be detected include at least one of the average particle size, the carbon content, aromaticity, heavy metal content, heavy metal composition, non-heavy metal impurity content, non-heavy metal impurity composition, or ash content of the coal. The characteristics of the coal may be detected using any suitable technique. Examples of techniques that may evaluate the coal include proximate and ultimate analysis (to detect at least one of moisture content, sulfur content, calorific value, volatile matter content, fixed carbon content, ash content, and elemental composition of the coal), thermogravimetric analysis, differential scanning calorimetry, scanning electron microscopy or other microscopy techniques, energy dispersive spectroscopy, or any other suitable characterization technique.

Evaluating the coal may assign at least one grade to the coal. The grade may include a numerical score, a number grade, a qualitative grade (e.g., best, intermediate, poor), or any other suitable grade. The grade may represent at least one of the coal's suitability to form life science devices, the coal's suitability to form a specific life science device, the yield (e.g., estimated amount of graphene that may be extracted from coal), the cost of extracting the graphene from the coal, the quality of the graphene extracted from the coal, how efficiently the graphene may be extracted from the coal using a specific extraction technique, which extraction technique may extract the graphene from the coal most efficiently, how efficiently the graphene extracted from the coal may be functionalized, how effective the extracted coal will be at detecting a specific target, or any other suitable criteria. The coal may be graded using many criteria and the coal may be assigned a single grade that represents a plurality of the criteria or a plurality of grades that represent different criteria.

In an example, coal that includes a relatively high hexavalent metal content may be assigned a high grade if the coal is to be used to form graphene for a biosensor since, as previously discussed, the hexavalent metal may allow the graphene extracted from the coal to be functionalized without negatively affecting the electrical properties of the graphene. The coal that includes the relatively high hexavalent metal content may be given a low grade if the coal is used in drug delivery system since the hexavalent metal may not be generally regarded as safe when administered to an individual. However, the coal that includes a high hexavalent metal content may be given a high grade even if the coal is used as a drug delivery system if the hexavalent metal is able to be removed from the graphene. Other impurities naturally present in the coal may also affect the grade since the impurities that remain in the graphene may be beneficial and/or detrimental. Examples of impurities that may be present in the coal that also remain in the graphene can include one or more of cadmium, selenium, boron, nitrogen, or silicon. In other examples, the coal may be given a high grade if the coal includes a high carbon content and, more preferably, a high aromatic carbon content since such values may indicate that a relatively large quantity of graphene may be extracted from the coal.

In an example, the grading may be used to select the coal used in block 104 (i.e., extract graphene from coal) for a predetermined extraction technique and/or used to form a specific life science device. In an example, the grading may be used to select the extraction technique and/or the parameters (e.g., temperature, duration, acid composition, catalyst composition, etc.) of the extraction technique to ensure the most efficient extraction of graphene from the coal. In an example, the grading may be used to select the life science device formed using the coal. In an example, the grading may be used to sort the coal, separate the coal, and/or selected which coal is discarded.

After block 102, the method 100 includes block 104. Block 104 includes extracting graphene from the coal. Extracting the graphene from the coal may include extracting the graphene that is naturally occurring in the coal. Extracting the graphene from the coal may also include forming graphene from the graphite, other aromatic carbon sources, or other carbon sources present in or formed from the coal. The graphene may be extracted from the coal using any suitable technique. Examples of techniques that may extract the graphene from the coal include, but are not limited to, the Hummers method, a modified Hummers method, exfoliation of the graphite formed from or extracted from the coal, and Staudenmeier-Hoffman-Hamdi method. These methods allow graphene to be produced from the coal through a process allowing for the ability to form reproducible high-quality graphene.

The Hummers method includes mixing the coal with a catalyst, such as sodium nitrate, and sulfuric acid to form a mixture. The mixture is heated to a first temperature of about 60° C. to about 70° C. The mixture is then cooled to a second temperature of about −5° C. to about 5° C. After cooling the mixture, a second catalyst, such as potassium permanganate, is added to the mixture. The mixture is then diluted with water. The solids, which include graphene and graphene oxide, are removed from the mixture.

The modified Hummers method may include any method that is similar to but different than the Hummers method. In some examples, the modified Hummers method may include heating the mixture to a first temperature that is less than 60° C. (e.g., about 30° C. to about 40° C., about 35° C. to about 45° C., about 40° C. to about 50° C., about 45° C. to about 55° C., or about 50° C. to about 60° C.) or greater than 70° C. (e.g., about 70° C. to about 80° C., about 75° C. to about 85° C., about 80° C. to about 90° C., about 85° C. to about 95° C., or about 90° C. to about 100° C.). In some examples, the modified Hummers method may include cooling the mixture to a second temperature that is less than −5° C. (e.g., about −30° C. to about −20° C., about −25° C. to about −15° C., about −20° C. to about −10° C., or about −15° C. to about −5° C.) or greater than 5° C. (e.g., about 5° C. to about 15° C., about 10° C. to about 20° C., about 15° C. to about 25° C., about 20° C. to about 30° C., about 25° C. to about 35° C., or about 30° C. to about 40° C.). In some examples, the modified Hummers method may include omitting one or more of sodium nitrate or potassium permanganate from the method. In some examples, the modified Hummers method may include using additional catalysts instead of or in conjunction with the sodium nitrate or potassium permanganate, such as potassium ferrate or hydrazine hydrate. In some examples, the modified Hummers method may include using an acid other than sulfuric acid (e.g., nitric acid, perchloric acid, chloric acid, chromic acid, hydrogen peroxide, etc.) or using a mixture of sulfuric acid and another acid. The parameters (e.g., temperature, catalyst composition, acid composition, etc.) may be selected based on the characteristics of the coal that was previously determined and the grading of the coal, as previously discussed.

In some examples, block 104 may include exfoliating the graphite present in the coal to extract the graphene. Exfoliating the graphite includes separating the weakly bonded graphene layers of the graphite to extract the graphene, for example by electrical, chemical, and/or mechanical exfoliation. The graphite may be exfoliated using any suitable technique, such as at least one of liquid-phase exfoliation, electrochemical exfoliation, or micromechanical exfoliation.

Other techniques may extract graphene from coal. In some examples, graphene may be extracted from coal using coal or a coal-derived carbon source in a CVD process. In an embodiment, graphene may be extracted from coal using coal or a coal-derived carbon source in a flash Joule heating device. In some examples, any other suitable technique may extract graphene from coal.

As previously discussed, the extraction techniques and the parameters of the extraction techniques used to extract graphene from the coal may be determined from evaluating the coal and/or the grading of the coal. Generally, the extraction technique and the parameters of the extraction technique may be selected to improve yields, decrease costs, decrease processing time, scalability, form graphene exhibiting certain characteristics, or form graphene exhibiting a certain quality (e.g., uniformity of characteristics).

In some examples, block 104 may include reducing the graphene to remove oxygen and oxygen-containing groups therefrom, forming graphene exhibiting specific properties. For example, some techniques disclosed herein may form graphene oxide in addition to or instead of graphene. The graphene may be reduced using any suitable technique, such as chemically reducing the graphene, exposing the graphene to hydrogen plasma, or exposing the graphene to strong light. However, as discussed in more detail below, the oxygen and oxygen-containing groups may not be removed from the graphene since, in some examples, graphene oxide may be used instead or in conjunction with graphene.

After block 104, the method 100 may include evaluating the graphene to detect one or more characteristics of the graphene. The characteristics that are detect may include one or more of the flake size, purity, average number of layers (e.g., is the graphene single layered or multi-layered), the quantity and composition of impurities (e.g., non-carbon elements or compounds), the electrical properties, or thermal properties of the graphene. Examples of techniques that may analyze the graphene include, but are not limited to, sieves and microscopy to determine flake size and the average number of layers; energy dispersive spectroscopy or other characterization techniques to detect and quantify impurities; voltmeters, current sensor, multimeters, or other electrical sensors to detect the electrical properties of the graphene; or thermogravimetric analysis, differential scanning calorimetry, or other thermal properties detection techniques.

In some examples, the graphene may be graded because of the evaluation. For example, the graphene may be graded based on the quality (e.g., uniformity of properties or closeness to desired properties), electrical properties, thermal properties, or any of the other detected characteristics thereof. The graphene may be sorted based on the grading thereof. The graphene may also be selected for use in a life science device based on the provided grade. In some embodiments, graphene may be discarded if the grade is sufficiently low.

After or concurrently with block 104, the method 100 may include functionalizing the graphene to attach or bond at least one functionalization group to the graphene. When the graphene is used in a biosensor, the functionalization groups may form all of at least one binding site of the biosensor or the functionalization groups may form a portion of the binding site (e.g., the binding site includes the functionalization group and a sensitive biological element). The binding site of the biosensor is configured to bind or otherwise react with at least one target that is to be detected (e.g., an analyte, virus, antibody to the virus, bacteria, etc.). When the graphene is used in a drug delivery system, the functionalization groups may form all of or at least a portion of the at least one binding site. The binding site of the drug delivery system may be configured to bind with or otherwise react with a selected organism (e.g., selected organ, cancerous cells, etc.) and/or the medicament. As previously discussed, impurities, such as hexavalent metals in the graphene may facilitate the functionalization of the graphene.

Examples of functionalization groups that may be bonded or added to the graphene include at least one of chromium tricarbonyl ($Cr(CO)_3$), molybdenum disulfide ($MoS_2$), hexagonal boron nitride (BN), transition metal dichalcogenides, an eta-6 ligand, for example including one or more heavy metals, oxi- and/or amine functionalization groups, or graphene quantum dots. The functionalization groups may be added to the graphene in any manner, as known in the art or as developed in the future. Examples of functionalization groups that may be added to the graphene and methods that may attach the functionalization groups to the graphene are disclosed in Nihar Mohanty and Vikas Berry, *Graphene-Based Single-Bacterium Resolution Biodevice and DNA Transistor: Interfacing Graphene Derivatives with Nanoscale and Microscale Biocomponents,* 8 Nano Letters 4469 (2008), the disclosure of which in incorporated herein by reference, in its entirety.

In some examples, only a single functionalization group is attached to the graphene. In such an example, the graphene may only detect one target or a plurality of undistinguishable targets. In some examples, a plurality of functionalization groups (e.g., about 2 to about 6, about 4 to about 8, about 6 to about 10, about 8 to about 15, about 10 to about 20, about 15 to about 30, about 25 to about 50, about 40 to about 70, or about 60 to about 100), such as different functionalization groups, may be added to the graphene, such as to the same graphene flake. In such examples, the graphene may detect a plurality of targets simultaneously. In some examples, the graphene is separated into a plurality of different groups of graphene that each include at least one flake of graphene. Each of the different groups of graphene may be functionalized with different functionalization groups. There may or may not be overlap between the different groups of graphene and the different functionalization groups. After functionalization, the different groups of graphene may detect different targets. The different graphene groups may form a plurality of subsensors on an array, wherein at least some of the subsensors are configured to detect different targets.

In some examples, the graphene formed during block 104 is not functionalized. The graphene may not be functionalized when the impurities, folds, or wrinkles in the graphene already form functionalization groups or binding sites for targets, when the sensitive biological element may be attached directly to the graphene, or when the biosensor is evaluated using techniques that do not require functionalization groups (e.g., Raman based detection detects the target based on the chemical structure of the targets).

In some examples, after block 104, the sensitive biological element is attached or bonded to the graphene. The sensitive biological element may be attached to the graphene indirectly via the one or more functionalization groups or may be directly attached to the graphene. The sensitive biological element may be attached to the graphene using any suitable technique, such as exposing the sensitive biological target to the graphene while a stimulus is or is not applied to the graphene. In some examples, the sensitive biological element includes an antibody to the target. In some examples, the sensitive biological element includes single strand of DNA configured to bind or otherwise react with a specific corresponding DNA strand or molecule (e.g., denatured DNA having a specific sequence). In an example, the sensitive biological element includes tissue, microorganism, organelles, cell receptors, enzymes, other forms of DNA or RNA< or other elements that bind or otherwise react with the target.

Figure 2:
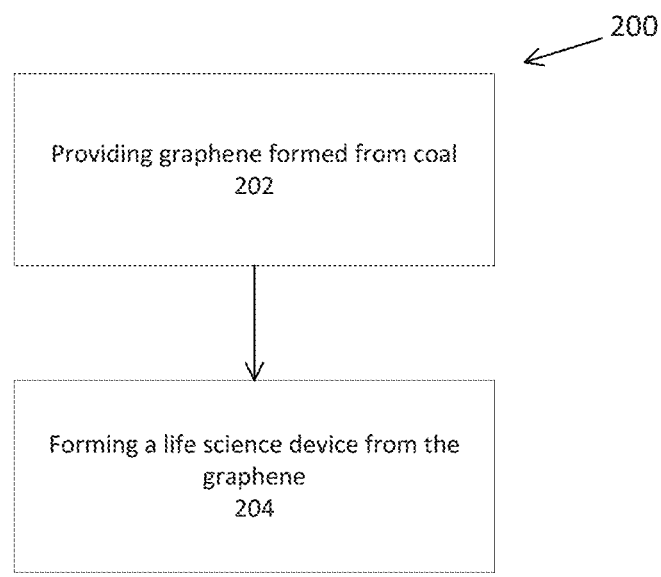
FIG. 2 is a flow chart of a method of forming one or more life science devices using graphene derived from coal.

FIG. 2 is a flow chart of a method 200 of forming one or more life science devices using graphene derived from coal. As shown in FIG. 2, the method 200 includes block 202, which includes providing graphene formed from coal, for example as described with respect to the method 100. The method 200 also includes block 204, which includes forming a life science device from the graphene. In some examples, one or more of the blocks 202 and/or 204 may be performed in a different order, eliminated, divided into additional acts, modified, supplemented with other acts, or combined into fewer acts.

Block 202 includes providing graphene formed from coal. The graphene that is provided may be formed using the method 100. For example, the graphene that is provided may include the graphene that is formed after block 104, after functionalizing the graphene, and/or after attaching the sensitive biological element to the graphene. In some examples, the graphene is provided from at least one first party (a manufacturer of the graphene) to at least one second party (a manufacturer of the life science device). In an embodiment, the graphene is manufactured by the same party that makes the life science device. Regardless, the method 200 may be an extension of the method 100 so the methods 100 and 200 form a single method.

In some examples, if the graphene is not evaluated, functionalized, and/or attached to the sensitive biological element before block 202, the method 200 may include evaluating, functionalizing, and/or attaching the sensitive biological element to the graphene. For example, the method 200 may include evaluating, functionalizing, and/or attaching the sensitive biological element to the graphene before, during, or after block 204.

After block 202, the method 200 may include block 204, which includes forming a life science device from the graphene. In some examples, block 204 includes forming a biosensor. The biosensor may include a rapid diagnostic biosensor, a sequencing biosensor, a cancer detection biosensor, a biosensor configured for personalized medicine, an enzyme-linked immunosorbent assay reporter, or any other biosensor. The biosensor may detect many targets, such as D-seine, deoxynuclieic acid hybridization, coronavirus disease 2019 (COVID-19) virus or antibodies for coronavirus disease 2019 virus, severe acute respiratory syndrome coronavirus (SARS) and/or antibodies for the severe acute respiratory syndrome coronavirus, other coronaviruses and/or antibodies for the other viruses, coronaviruses, zika virus, *Borrelia burgdorferi* and/or *Borrelia mayonii* (i.e., the bacteria that causes lyme disease), influenza A virus, influenza B virus, or other biomarkers. The biosensors disclosed herein may be more sensitive, specific robust, hardy, as well as potentially offering usage in more applications than existing biosensors while also being cheaper than biosensors that included graphene formed using conventional methods and sources, such as a sandwich assay.

In some examples, block 204 may include forming a drug delivery system from the graphene. For example, block 204 (i.e., forming a life science device from the graphene) may include rolling the graphene to form CNTs. The CNTs includes one or more binding sites formed thereon. Similar to the biosensors disclosed herein, the binding sites of the CNTs are formed by at least one functionalizing the CNTs (either before or after rolling the graphene into the CNTs) using the techniques disclosed, wrinkles or folds present in the graphene, or the impurities naturally present in the coal. In some examples, the binding sites may be configured to bind or otherwise react with the target organism (e.g., cancer cells, a particular organ, etc.). In an example, the binding sites may also be configured to bind or otherwise react with the medicament that the CNTs are configured to provide to the target organism.

The CNTs can deliver drugs to specific cells, such as cancer cells thereby reducing the amount of cancer drugs—in dosage, and in number of treatments—given to an individual, thus increasing the efficiency of treatment, and decreasing side-effects. The CNTs may also cross the blood-brain barrier. Further, the CNTs may have low cellular toxicity and low cost relative to some drug delivery systems.

Figure 3A:
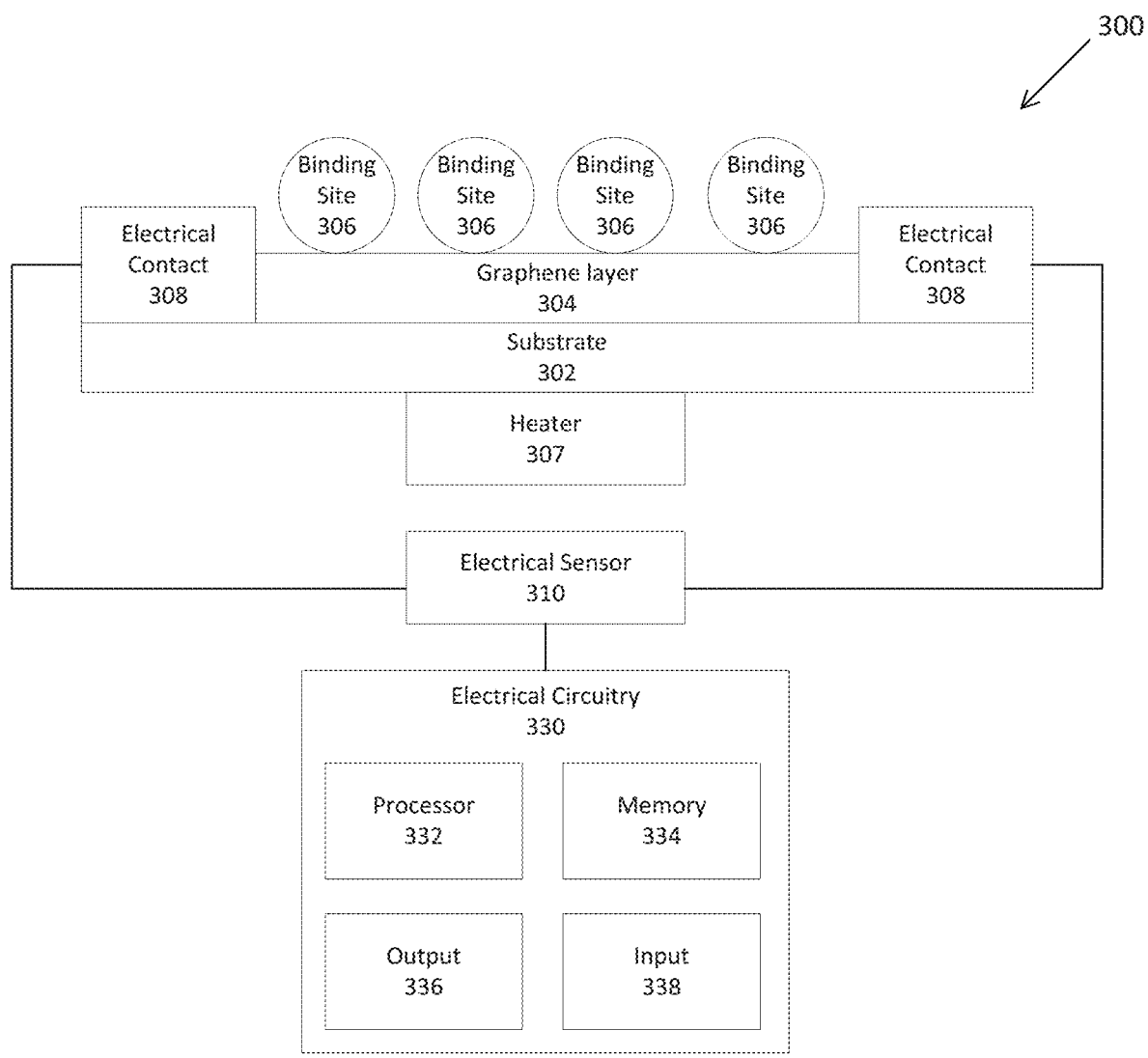
FIG. 3A is a schematic cross-sectional view of a biosensor.

FIG. 3A is a schematic cross-sectional view of a biosensor 300. The biosensor 300 includes a substrate 302. The substrate 302 may include, for example, silica, silicon, a metal, or any other suitable material. The substrate 302 may also include a single material (as shown) or may be formed from multiple layers (e.g., a base with at least one layer disposed thereon). At least one graphene layer 304 may be disposed on at least a portion of at least one surface of the substrate 302. In some examples, up to about 5 layers, 10 layers, 15 layers, 20 layers, can be disposed on the surface of the substrate 302. The graphene layer 304 may be disposed on the substrate 302 using any suitable method. For example, the graphene layer 304 may be disposed in a solution and the solution may be applied to the substrate 302 using a spin coating technique. One or more binding sites 306 configured to bind with or otherwise react with a target may be formed on the graphene layer 304. As previously discussed, the binding site 306 may be formed by at least one of functionalizing the graphene layer 304, attaching (i.e., directly or indirectly) one or more sensitive biological elements to the graphene layer 304, wrinkles or folds formed in the graphene layer 304, or impurities naturally present in the graphene layer 304. When the biosensor 300 includes a plurality of binding sites 306, each of the binding sites 306 may be the same or at least one of the binding sites 306 may differ from at least one other binding site 306.

The biosensor 300 may also include a heater 307 configured to heat at least the substrate 302 and the graphene layer 304. In an embodiment, the heater 307 may cause the target that is bound or otherwise reacted with the binding sites 306 to be released from the binding sites 306 by heating the graphene layer 304 allowing the biosensor 300 to be reused. In some examples, when the target is DNA, heat from the heater 307 may cause the DNA to denature allowing the DNA to bind or react with the binding site 306 (e.g., the binding site 306 includes a single strand DNA).

Figures 6A, 6B:
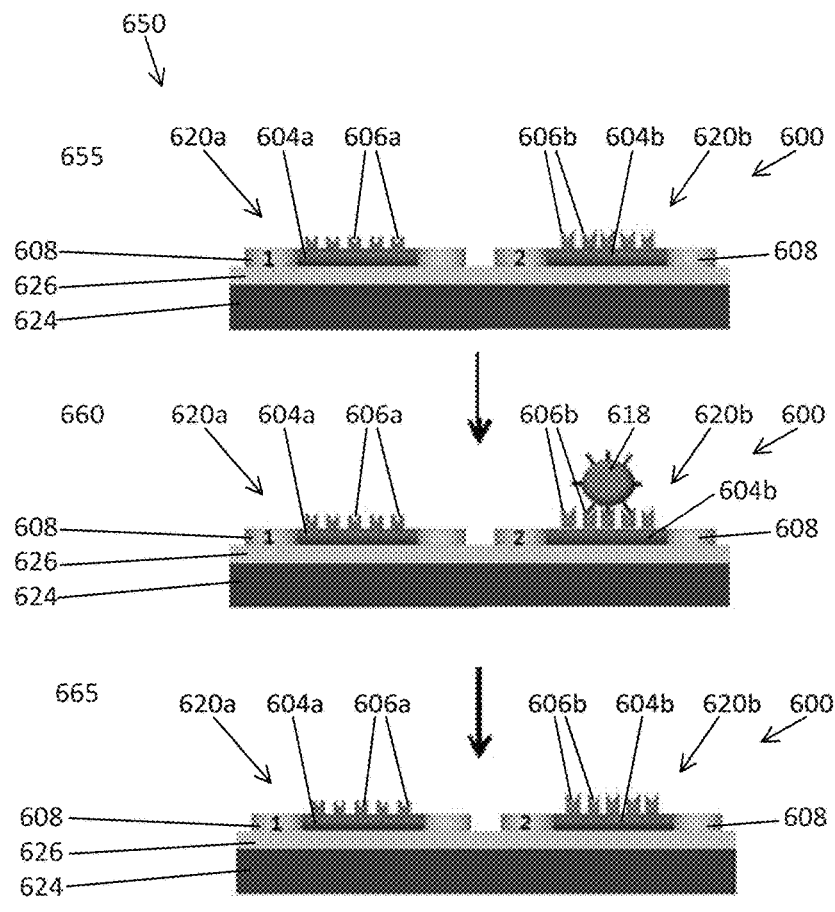
FIG. 6A is a schematic cross-sectional view of a biosensor that includes a plurality of subsensors and a method of using the biosensor.
FIG. 6B is a graph illustrating the electrical properties of the first and second subsensor during a recognition event.

In some examples, the biosensor 300 includes two or more electrical contacts 308 (e.g., electrodes or probes) contacting at least a portion of the graphene layer 304. The electrical contacts 308 may also contact the substrate 302. The electrical contacts 308 may be connected to an electrical sensor 310 via one or more wires or other electrical connections. The electrical sensor 310 may include any sensor configured to detect one or more electrical characteristics of the graphene layer 304. For example, the electrical sensor 310 may include a voltmeter, a current sensor, a multimeter, or any other sensor that can detect the electrical characteristics of the graphene layer 304. For example, the electrical properties of the graphene layer 304 may change after the graphene layer 304 is exposed to the target (as shown in FIG. 6B). How the electrical properties of the graphene layer 304 changes depends at least partially on the binding site 306 and the particular target. For example, the electrical current may change (i.e., the biosensor 300 is an amperometric biosensor), medium conductance may change (i.e., the biosensor 300 is a conductometric biosensor), the potential or charge accumulation may change (i.e., the biosensor 300 is a potentiometric biosensor), the interfacial electrical impedance may change (i.e., the biosensor 300 is a impedimetric sensor), or the current or potential across a semiconductor channel may change (i.e., the biosensor 300 is a field-effect transistor).

The biosensor 300 includes electrical circuitry 330. In some examples, as shown, the electrical circuitry 330 is coupled to the electrical sensor 312 (e.g., via an input of the electrical circuitry 330). In some examples, the electrical circuitry 330 is integrally formed with the electrical sensor 312. Regardless, the electrical circuitry 330 is configured to receive one or more signals from the electrical sensor 312. The signals from the electrical sensor 312 include the detected electrical properties of the graphene layer 304 and the electrical circuitry 330 is configured to analyze the detected electrical properties to determine if the target is present. For example, the electrical circuitry 330 includes at least one processor 332 and non-transitory memory 334 coupled to the processor 332. The non-transitory memory 334 includes one or more operational instructions stored thereof and the processor 332 is configured to execute the operational instructions. The operational instructions, in conjunction with the signals received from the electrical sensor 312, allows the electrical circuitry 330 to determine the presence and/or quantity (e.g., concentration) of the target on the graphene layer 306. For example, with the operational instructions, the processor 332 may determine the presence and/or quantity of the target on the graphene layer 306 by determining that the detected electrical properties include a current change, a medium conductance change, a potential or charge accumulation change, an interfacial electrical impedance change, or a current or potential across semiconductor channel.

The electric circuitry 330 may also include or be connected to an output 334 that allows the electrical circuitry 330 to communicate with an individual using the biosensor 300. The output device 334 may include a display, one or more lights, a tactile feedback device, or any other suitable output device. The electrical circuitry 334 may be configured, through the output device 334, to provide graphic and/or tabular information to the individual, a yes or a no that the target is present or present over a certain quantity, the binding affinity (antibody/antigen) or mismatch of nucleic acids, the concentration of the target, or any other information. In an embodiment, the electrical circuitry 330 may also include or be connected to an input 336 that allows a user to provide commands to the electrical circuitry 330, such as instructions to analyze a sample, which information to provide through the output 334, or information regarding the user. The input 336 may include a touch screen, a mouse, a keyboard, one or more buttons, or any other suitable input device.

The biosensor 300 may include one or more components that are not shown. In some examples, the biosensor 300 may include a housing that includes one or more components of the biosensor 300 disposed therein or thereon. The housing may be small enough to be easily held in a hand. In some examples, the biosensor 300 may include one or more stimulus devices (e.g., ultraviolet light source) that are configured to provide a stimulus that causes the target to be released from the binding sites. In some examples, the biosensor 300 may include a power source, such as batteries or a plug, that provides electrical power to one or more components (e.g., electrical sensor 310 and/or electrical circuitry 330) of the biosensor 300.

Figure 3B:
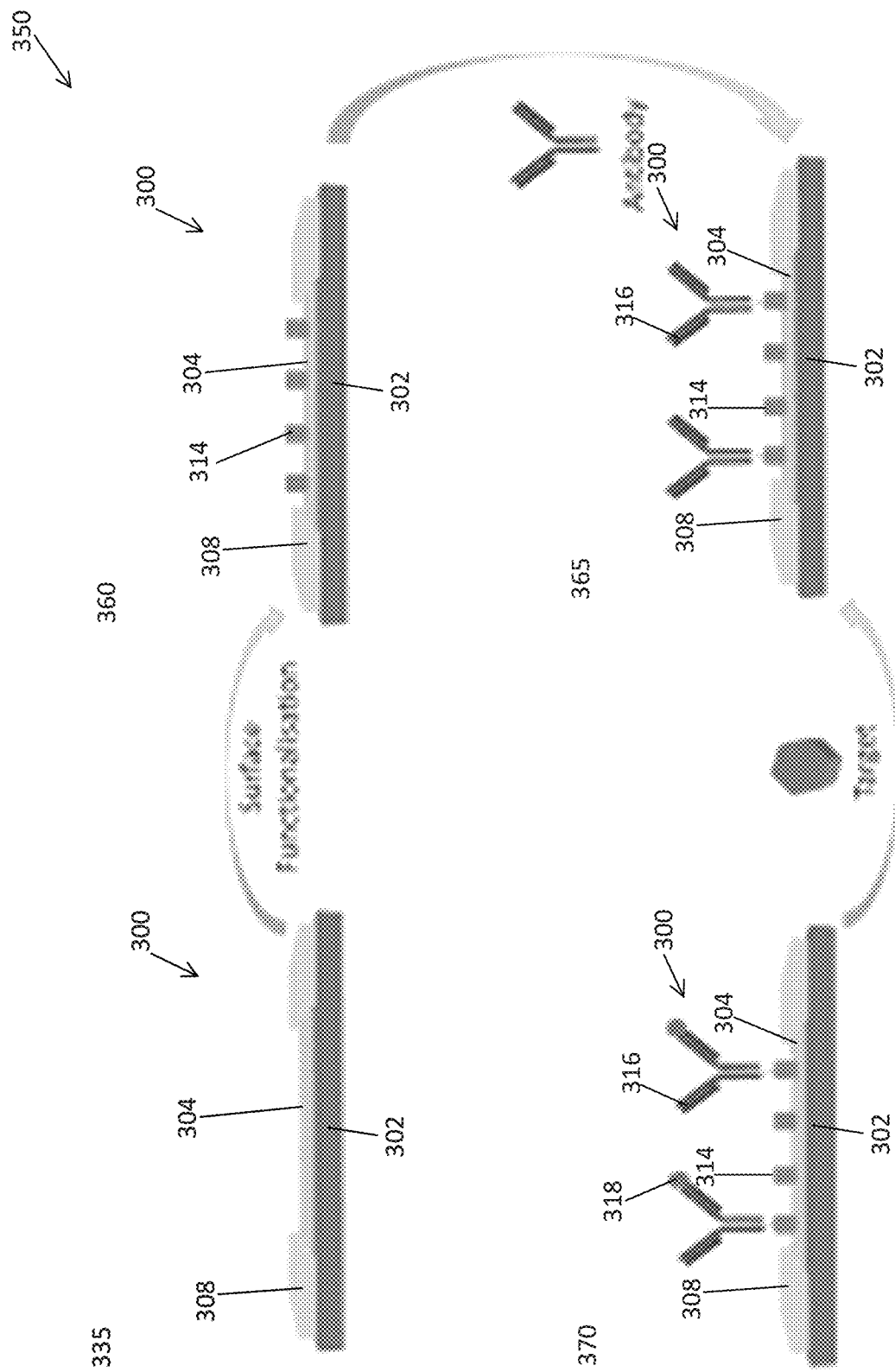
FIG. 3B schematically illustrates a method of forming and using a biosensor.

FIG. 3B schematically illustrates a method 350 of forming and using biosensor 300. As shown in block 355, the method 350 can include providing the substrate 302. In the illustrated example, the substrate 302 is provided with the graphene layer 304 and the electrical contacts 308 already formed thereon. However, block 355 may include disposing the graphene layer 304 and/or the electrical contacts 308 on the substrate 302. The method 350 can also include 360, for example after block 355. Block 360 includes functionalizing the graphene layer 304 by attaching one or more functionalization groups 314 to the graphene layer 304. However, as previously discussed, block 360 may be omitted from the method 350 if the graphene was previously functionalized or if the graphene will not be functionalized. Block 360 may be followed by block 365. Block 365 includes attaching one or more sensitive biological elements 316 (labeled as antibody in the figure, although any biological element can be used as described herein) to the graphene layer 304. As shown, the biological elements 316 may be indirectly attached to the graphene layer 304 via the functionalization groups 314. However, as previously mentioned, the sensitive biological elements 316 may be attached directly to the substrate 304 (e.g., the functionalization groups 314 are omitted from the biosensor 300). After block 365, the method 300 may include block 370. Block 370 includes using the biosensor 300 to detect a target 318 in a sample (not shown). The sample may include, for example, blood, saliva, blood and/or saliva in a diluent, breath, any other material that may include the target, or combinations thereof. Block 370 may include exposing at least a portion of the graphene layer 304 to the sample. If the sample includes the target 318, the target 318 will bind or otherwise react with the binding sites (e.g., the functionalization groups 314 and/or the sensitive biological element 316). Binding or otherwise reacting the target 318 to the binding sites changes the electrical properties of the graphene layer 304. In some embodiments, the sample will be removed from the graphene layer 304 (e.g., the biosensor 300 is washed) to prevent the sample from changing the electrical properties of the graphene layer 304. Removing the sample will not remove the target 318 that is bounded to or otherwise reacted with the binding sites. The electrical properties may then be detected using the electrical sensor 310 (shown in FIG. 3A).

Referring back to FIG. 3A, in some examples, one or more of the electrical contacts 308 or the electrical sensor 310 may be omitted from the biosensor 300. In some examples, the substrate 302, the graphene layer 304, the binding sites 306, and, optionally, the electrical contacts 310 may form a cartridge attached to the rest of the biosensor 300. The cartridge may decrease the cost of using the biosensor 300 since the electrical sensor 310 and the electrical circuitry 311 may be reused. The cartridge may also allow the biosensor 300 to detect multiple targets since the biosensor 300 may be configured to be used with different cartridges configured to detect different targets (e.g., the cartridges are interchangeable). In some examples, the biosensor 300 may configured to be analyzed using a device other than the electrical sensor 310. For example, the biosensor 300 may be configured to be analyzed using Raman spectroscopy, microscopy, other similar characterization technique that can detect the target. In such an example, the biosensor 300 may bind or otherwise react the target with the binding sites 306. Optionally, the biosensor 300 may be cleaned but, since the target is bounded or reacted with the binding sites 306, the cleaning does not remove the target from the biosensor 300. Raman spectroscopy, microscopy, or other similar characterization techniques can then be used to analyze the biosensor 300 to determine if the target is present on the biosensor 300.

Figure 4:
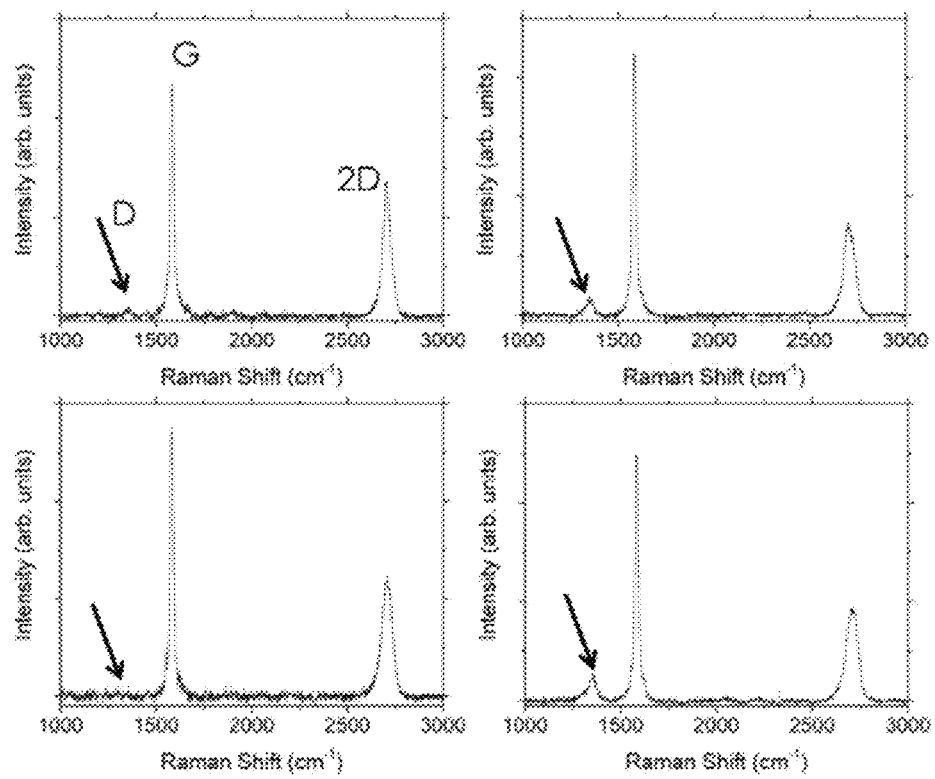
FIG. 4 shows Raman spectrographs of graphene derived from coal.

FIG. 4 shows Raman spectrographs of graphene formed from coal according to the methods described herein. The Raman spectrographs shown in FIG. 4 were generated using samples of graphene formed by a CVD process using a coal-derived carbon source. The arrows in the graphs of FIG. 4 indicate the location of the "D band" of graphene. Generally, the "D band" of graphene in Raman spectrographs are associated with defect states in the graphene structure. The graphs of FIG. 4 illustrate that the "D band" is non-existent or minimal indicating that the graphene exhibits substantially no undesirable defects. The graphs illustrated in FIG. 4 may be baselines to determine if the biosensor 300 includes a desired level or impurities, the target molecule, or any other additional components. For example, Raman spectrographs that differ significantly from the graphs illustrated in FIG. 4 (e.g., including additional peaks and/or a change in the relative heights of the peaks) may indicate the presence of desired levels of impurities in the graphene as described herein.

Figure 5:
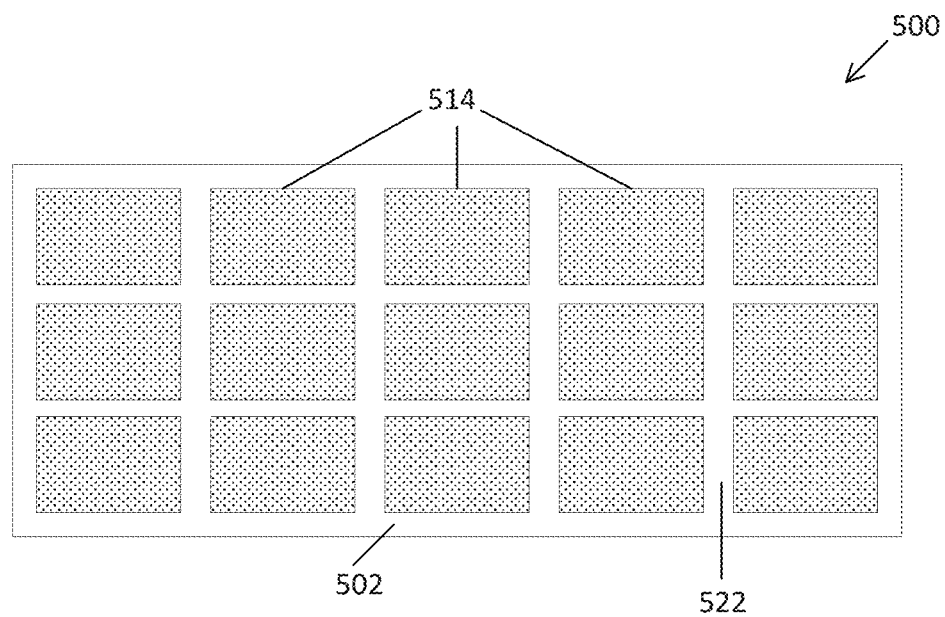
FIG. 5 is a schematic top plan view of a biosensor including an array.

In some examples, the biosensors disclosed herein may form an array. FIG. 5 is a schematic top plan view of a biosensor 500 that is an array. The biosensor or biosensors forming the array can be the same or substantially similar to any of the biosensors disclosed herein. For example, the biosensor 500 includes a substrate 502. The biosensor 500 includes a plurality of subsensors 520 (shown textured) formed on the substrate 502. Each of the subsensors 520 includes at least one graphene layer and one or more binding sites that are the same or substantially similar to any of the graphene layers or binding sites disclosed herein and may be formed according to any of the methods disclosed herein. Each of the subsensors 520 may be separated from each other by a gap 522. The gap 522 may be substantially free of graphene or substantially free of graphene that includes one or more binding sites. The gap 522 may be formed by masking a portion of the substrate 502 before depositing the graphene on the substrate 502, masking a portion of the graphene layer before the graphene layer is functionalized and/or attached to the sensitive biological element, the graphene layer is selectively formed around the gap 522, portions of the graphene layer are removed to form the gap 522, etc. When the biosensor 500 is configured to be analyzed using an electronic sensor (not shown), the electric contacts may be configured to be connected to each of the subsensors 520, some of the subsensors 520, the gap 522, or a combination of the gap 522 and at least one of the subsensors 520.

In some examples, at least one of the subsensors 520 is configured to bind with or react with a target that differs from at least one other subsensor 520. For example, the plurality of subsensors 520 may include at least one first subsensor and at least one second subsensor. The first subsensor may include one or more first binding sites configured to bind or otherwise react with a first target while the second subsensor does not include the first binding sites and may not detect the first target. However, in some example, the second subsensor may include one or more second binding sites configured to bind or otherwise react with a second target that differs from the first target. The first subsensor may not include the one or more second binding sites and may not detect the second target. The plurality of subsensors 520 may allow for the biosensor 500 to detect more targets than if the biosensor 500 only include one subsensor or a plurality of subsensors 520 that are all the same. At least some of the subsensors 520 may be different because, as previously discussed, the graphene used to form each subsensor 520 may be functionalized by different functionalization groups or have different sensitive biological elements attached thereto. It is noted that different sources of coal (e.g., coal from different regions, different mines, different seams, including different impurities) may also cause the graphene formed therefrom to bind or react with different targets. It is noted that, in some examples, at least two of the subsensors 520 may be the same which may allow the two subsensors 520 to confirm each other's results.

The biosensor 500 may include any suitable number of subsensors 520. For example, in the illustrated embodiment, the biosensor 500 includes 15 subsensors 520. However, it is noted that the biosensor 500 may include less than 15 subsensors 520 (e.g., 2, 3, 4, 5, 6, 7, 8, 9, 10, 11, 12, 13, 14, or ranges between any of these numbers) or greater than 15 subsensors 520 (e.g., 16 or greater, 25 or greater, 50 or greater, 75 or greater, 100 or greater, 16 to 30, 25 to 50, 40 to 70, or 60 to 100).

FIG. 6A is a schematic cross-sectional view of a biosensor 600 that includes a plurality of subsensors and a method 650 of using the biosensor 600. During block 655, the biosensor is provided. Except as otherwise disclosed, the biosensor 600 is the same or substantially similar to the biosensor 500. For example, the biosensor 600 includes a substrate. The substrate may include a base 624 and at least one layer 618 disposed on the base 624, though it is noted that the layer 618 may be omitted from the substrate. The biosensor 600 may include a first subsensor 620a and a second subsensor 620b disposed on the substrate. Each of the first and second subsensors 620a, 620b include a graphene layer 604 and at least two electrical contacts 608. The first and second subsensors 620a, 620b include different binding sites configured to bind or otherwise react with different targets. For example, the second subsensor 620b may include one or more second binding sites 606b that are configured to bind or otherwise react with a second target 618 while the first subsensor 620a may include one or more first binding sites 606a that are not configured to bind or otherwise react with the second target 618. Instead, the first binding sites 606a may be configured to bind or otherwise react with a first target (not shown).

During block 660, a sample (not shown) that may or may not include the second target 618 is applied to the biosensor 600. The second target 618 binds or otherwise reacts with the second binding sites 606b but does not bind or otherwise react with the first binding sites 606a. During block 665, the second target 618 may be released from the second binding sites 606b, as discussed above, thereby allowing the biosensor 600 to be reused.

FIG. 6B is a graph illustrating the electrical properties of the first and second subsensor 620a, 620b during each block of the method 650. The graphs plot the conductance of the first and second subsensors 620a, 620b over time. However, it is noted that the graph may plot any suitable electrical characteristics, such as electrical current over time, potential or charge accumulation over concentration of the target, interfacial electrical impedance, or drain current over drain-source voltage. As shown in FIG. 6B, during block 655, the electrical properties of the first and second subsensors 620a, 620b remain constant since the biosensor 600 is not exposed to the sample. However, during block 660, the conductance of the second subsensor 620b decreases because the second binding sites 606b bind or otherwise react with the target 618. However, the conductance of the first subsensor 620b remains unchanged since the first binding sites 606a do not bind or otherwise react with the target 618. During block 665, the conductance of the second subsensor increases since the target 618 is release therefrom.

The methods and life science devices disclosed here are disclosed as involving graphene. However, it is noted that the methods and life science devices disclosed herein may involve graphene oxide ("GO") and/or carbon nanodots (e.g., GO nanodots or graphene nanodots) instead of or in conjunction with graphene, without limitation. For example, some methods disclosed herein to form graphene may also form GO and/or carbon nanodots from coal instead of or in conjunction with graphene depending on the extraction techniques and the parameters of the extraction techniques. These GO and/or carbon nanodots derived from coal may be used in the life science devices instead of or in conjunction with the graphene since these GO and carbon nanodots derived from coal may be made from a cheap source (i.e., coal), may include beneficial impurities (i.e., hexavalent metals), and exhibit beneficial electrical and thermal properties.

For example, the biosensors disclosed herein may include GO layers, carbon nanodot layers, a combination thereof, or a combination of graphene and GO and/or nanodots. Regardless of whether these layers include graphene, GO, carbon nanodots, or a combination thereof, the layers of the biosensor may be functionalized and/or sensitive biological elements may be attached to these layers and the biosensor may be used as disclosed herein. Examples of GO quantum dots that may form biosensors are disclosed in Sukhyun Kang et al., *Graphene Oxide Quantum Dots Derived from Coal for Bioimaging: Facile and Green Approach,* 9 Sci Rep 4101 (2019), the disclosure of which is incorporated herein by reference, in its entirety.

Various inventions have been described herein with reference to certain specific embodiments and examples. However, they can be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

The foregoing description, for purposes of explanation, used specific nomenclature to provide a thorough understanding of the described embodiments. However, it can be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It can be apparent to one of ordinary skill in the art that many modifications and variations are possible in view of the above teachings.

What is claimed is:

1. A method to form a life science device, the method comprising:
    extracting an amount of graphene from coal, the graphene having at least one property at least partially dependent on a composition of the coal; and
    forming a life science device from the amount of graphene by disposing at least one graphene layer on a substrate to form a biosensor, the at least one graphene layer comprising one or more binding sites configured to bind or otherwise react with one or more targets;
    functionalizing at least some of the at least one graphene layer to form the one or more binding sites, wherein functionalizing at least some of the at least one graphene layer comprises functionalizing impurities naturally present in the graphene layer, wherein the impurities naturally present in the graphene layer comprise hexavalent metals.

2. The method of claim 1, wherein disposing the at least one graphene layer on the substrate comprises:
    disposing a first graphene layer on the substrate to form a first subsensor; and
    disposing a second graphene layer on the substrate to form a second subsensor that is spaced apart from the first subsensor;
    wherein the first graphene layer comprises a first binding site and the second graphene layer comprises a second binding site that is different from the first binding site.

3. The method of claim 1, further comprising forming one or more electrical contacts on the at least one graphene layer or the substrate.

4. The method of claim 1, further comprising attaching one or more sensitive biological elements to the at least one graphene layer.

5. The method of claim 1, wherein forming the life science device from the amount of graphene comprises rolling at least some of the amount of graphene into a carbon nanotube to form a drug delivery system.

6. A method of forming graphene for use in a life science device from coal, the method comprising:
    analyzing a characteristic of an amount of coal; and extracting an amount of graphene from the amount of coal, the graphene having at least one property at least partially dependent on the characteristic of the coal, wherein the characteristic of the coal comprises hexavalent metals present in the coal.

7. The method of claim 6, wherein extracting the amount of graphene from the amount of coal comprises extracting the graphene from the coal using the Hummers method or a modified Hummers method.

8. The method of claim 6, wherein extracting the amount of graphene from the amount of coal comprises exfoliating graphite that is present in the coal.

9. The method of claim 6, wherein the characteristic further comprises at least one of a carbon, aromaticity, heavy metal, or ash content of the amount of coal.

10. The method of claim 6, further comprising selecting one or more parameters of an extraction technique that is used to extract the amount of graphene from the amount of coal based at least partially on the characteristic.

11. The method of claim 6, further comprising evaluating the amount of graphene to determine a property of the graphene.

12. The method of claim 11, wherein the property comprises at least one of an average flake size, a graphene purity, an average number of carbon layers, a presence of impurities, a composition of the impurities, electrical properties, or thermal properties.

13. The method of claim 12, further comprising selecting at least some graphene exhibiting the property from the amount of graphene for use in the life science device.

14. The method of claim 6, further comprising functionalizing at least some of the amount of graphene.

15. The method of claim 6, further comprising forming at least some of the amount of graphene into the life science device.

16. A biosensor comprising:
a substrate;
a graphene layer disposed on the substrate, the graphene layer comprising graphene formed from coal and having a property at least partially dependent on a characteristic of the coal, wherein the graphene layer comprises a functionalization group including impurities naturally present in the graphene layer, wherein the impurities naturally present in the graphene layer comprise hexavalent metals; and
a binding site bonded to the graphene, the binding site configured to bind or otherwise react with one or more targets.

17. The biosensor of claim 16, further comprising a first subsensor and a second subsensor spaced apart from the first subsensor;
the first subsensor comprising a first binding site and the second subsensor comprising a second binding site that is different from the first binding site.

18. The biosensor of claim 16, wherein the biosensor comprises at least one of an amperometric biosensor, a conductometric biosensor, a potentiometric biosensor, impedimetric biosensor or a field-effect transistor biosensor.

19. The biosensor of claim 16, wherein the biosensor comprises at least one of a rapid diagnostic biosensor, a sequencing biosensor, a cancer detection biosensor, or a biosensor for personalized medicine.

20. The biosensor of claim 16, wherein the biosensor comprises an enzyme-linked immunosorbent assay.

* * * * *